(12) United States Patent
Hoffmann et al.

(10) Patent No.: US 7,678,750 B2
(45) Date of Patent: Mar. 16, 2010

(54) CLEANSING COMPOSITION COMPRISING A COATED SYNTHETIC FLUORPHOLOGOPITE AND A TERNARY SURFACTANT MIXTURE

(75) Inventors: Martin Hoffmann, Zwingenberg (DE); Ilka Tietjen, Sandhausen (DE)

(73) Assignee: KPSS-Kao Professional Salon Services GmbH, Darmstadt (DE)

( * ) Notice: Subject to any disclaimer, the term of this patent is extended or adjusted under 35 U.S.C. 154(b) by 82 days.

(21) Appl. No.: 11/924,901

(22) Filed: Oct. 26, 2007

(65) Prior Publication Data

US 2008/0125339 A1    May 29, 2008

(30) Foreign Application Priority Data

Nov. 24, 2006    (EP) .................................. 06024376

(51) Int. Cl.
*C11D 3/14* (2006.01)
*C11D 1/94* (2006.01)

(52) U.S. Cl. .................. 510/119; 510/123; 510/130; 510/422; 510/438; 510/441; 510/507; 510/511

(58) Field of Classification Search ................ 510/119, 510/123, 130, 422, 438, 441, 507, 511
See application file for complete search history.

(56) References Cited

U.S. PATENT DOCUMENTS

| 5,851,541 | A * | 12/1998 | Corey et al. .................. 424/401 |
| 6,716,440 | B2 * | 4/2004 | Aronson et al. ............. 424/401 |
| 6,968,849 | B2 | 11/2005 | Vena et al. |
| 7,524,336 | B2 | 4/2009 | Hoffmann |
| 2005/0044642 | A1 | 3/2005 | Butcher |
| 2005/0158268 | A1 * | 7/2005 | Schmucker-Castner et al. ................. 424/70.16 |
| 2005/0163730 | A1 * | 7/2005 | Rosevear et al. ............... 424/59 |
| 2005/0164896 | A1 * | 7/2005 | Dabkowski et al. .......... 510/123 |
| 2005/0227886 | A1 * | 10/2005 | Patel et al. .................... 510/141 |
| 2005/0233916 | A1 * | 10/2005 | Polonka et al. .............. 510/130 |
| 2005/0233917 | A1 * | 10/2005 | Shiloach et al. ............. 510/130 |
| 2006/0277694 | A1 | 12/2006 | Kleen et al. |
| 2007/0048239 | A1 * | 3/2007 | Song et al. ..................... 424/63 |
| 2008/0118452 | A1 * | 5/2008 | Hollman et al. ............... 424/61 |
| 2008/0160056 | A1 * | 7/2008 | Boyd et al. .................. 424/401 |

FOREIGN PATENT DOCUMENTS

| WO | 0128508 A1 | 4/2001 |
| WO | 2005058261 A1 | 6/2005 |
| WO | 2005065632 A1 | 7/2005 |
| WO | 2006118940 A1 | 11/2006 |

* cited by examiner

*Primary Examiner*—Charles I Boyer
(74) *Attorney, Agent, or Firm*—Norris McLaughlin & Marcus, PA

(57) ABSTRACT

The present invention is related to an aqueous cleansing composition especially for keratin fibers such as human hair with shine enhancing effect. More specifically subject matter of the present invention is an aqueous cleansing composition especially for keratin fibers such as human hair comprising one or more surfactant selected from anionic, non-ionic and amphoteric ones at a concentration of 5 to 50% by weight calculated to total composition, wherein the composition does not comprise any monoethanolamide surfactant, and at least one color effect pigment consisting of synthetic mica coated with metal oxide or oxides and having a volume particle size distribution in the range of 1 to 750 μm at a concentration of 0.01 to 10% by weight, calculated to total composition.

7 Claims, No Drawings

CLEANSING COMPOSITION COMPRISING A COATED SYNTHETIC FLUORPHOLOGOPITE AND A TERNARY SURFACTANT MIXTURE

The present invention is related to an aqueous cleansing composition especially for keratin fibres such as human hair with shine enhancing effect.

Cleansing compositions have been known for many years. Many patent applications and scientific publications deal with such compositions aiming at cleansing and especially improving conditioning effects wherein shine enhancing of human hair has gained particular attention. Although this, there is still need for improvement.

Hair shine improvement has been one of the main areas of development. Hair shine is very much related to the surface structure of hair and this varies very much with the degree of damage either by environmental effects or chemical treatment of hair such as permanent shaping or oxidative colouring. Although consumers with healthy non-damaged hair are generally satisfied with hair shine, shine of damaged hair is usually found to be unsatisfactory. There have been studies aiming improving shine of especially damaged hair.

Present inventors have surprisingly found out that a cleansing composition comprising one or more surfactants and a colour effect pigment of synthetic mica coated with metal oxide or oxides cleanses hair thoroughly and improves shine and conditions hair excellently in terms of combability, elasticity, smoothness and softness.

"Accordingly the subject of the present invention is an aqueous cleansing composition especially for keratin fibers such as human hair comprising one or more surfactant selected from anionic, non-ionic and amphoteric ones at a concentration of 5 to 50% by weight calculated to total composition, wherein the composition does not comprise any monoethanolamide surfactant, and at least one color effect pigment consisting of synthetic mica coated with metal oxide or oxides and having a volume particle size distribution in the range of 1 to 750 μm at a concentration of 0.01 to 10% by weight, calculated to total composition."

Use of synthetic mica coated with metal oxide or oxides mainly in decorative cosmetics is disclosed in an international patent application of Sun Chemical Corporation published with a number WO 2005/065632 A1. In the document synthetic mica and coated synthetic mica with at least one metal oxide or oxides is disclosed in detail, the content of the document is included herewith by reference. It also discloses a cleansing composition comprising monoethanolamide surfactant in addition to other surfactants.

Suitable metal oxide or oxides for coating synthetic mica are titanium dioxide, chromium oxide, ferric oxide or mixtures thereof. In the present invention the preferred is synthetic mice coated with titanium dioxide. Such materials are commercially available from Sun Chemical Corporation and known with their INCI names Synthetic Fluorphologopite.

The particle size distribution of synthetic mica coated with a metal oxide or oxides is in the range of 1 to 750 μm, preferably 1 to 250 μm, more preferably 1 to 100 μm and most preferably 20 to 95 μm. The particle sizes referred are relating to the volume particle size distribution meaning that particles found in the coated synthetic mica having volume particle size in the given ranges.

Concentration of synthetic mica coated with at least metal oxide or oxides is from 0.001 to 10%, preferably 0.05 to 7.5%, more preferably 0.1 to 5% and most preferably 0.25 to 2.5% by weight calculated to total composition.

Cleansing compositions of the present invention can be in the form of conventional liquid thickened shampoo, as well in the form of ready to use foam, delivered either from a pump-foamer or from an aerosol bottle. In the case that an aerosol foam preparation is preferred, propellant gas must be added to the formulation. The suitable propellant gasses are carbondioxide, dimethylether and alkanes such as butane propane or their mixtures.

Cleansing compositions of the present invention comprise at least one surfactant selected from anionic, non-ionic and/or amphoteric or zwitterionic surfactants at a concentration range of 5 to 50%, preferably 5 to 40% and more preferably 7.5 to 30%, and most preferably 10 to 25% by weight, calculated to the total composition.

In an embodiment of the present invention cleansing composition of the present invention, comprises at least one anionic, at least one nonionic surfactant. More preferably the compositions further comprise additionally at least one amphoteric surfactant.

Anionic surfactants suitable within the scope of the invention are preferably present in an amount from 1 to about 30%, preferably 2 to 20% and most preferably 2-15%, and most preferably 2 to 10% by weight, calculated to the total composition.

In principal any anionic surfactant is suitable within the meaning of the present invention. Nonlimiting examples are anionic surfactants of the sulfate, sulfonate, carboxylate and alkyl phosphate type, especially, of course, those customarily used in shampoo compositions, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates constituting mild, skin-compatible detergents.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula

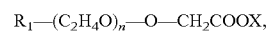

wherein $R_1$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

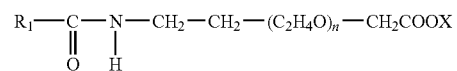

wherein $R_1$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

It is also possible to use mixtures of several anionic surfactants, for example an ether sulfate and a polyether carboxylic acid or alkyl amidoether carboxylic acid.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N-$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

The most preferred anionic surfactants within the meaning of the present invention are those of alkyl ether sulphates such as lauryl ether sulphate and aminocarboxylic acids such as lauroyl glutamate sodium salt.

Further surfactants in the shampoo compositions according to the invention are nonionic surfactants in admixture with anionic surfactants. Especially suited are alkyl polyglucosides of the general formula $$R_2\text{—}O\text{—}(R_3O)_n\text{-}Z_x,$$

wherein $R_2$ is an alkyl group with 8 to 18 carbon atoms, $R_3$ is an ethylene or propylene group, Z is a saccharide group with 5 to 6 carbon atoms, n is a number from 0 to 10 and x is a number between 1 and 5.

These alkyl polyglucosides have recently become known in particular as excellent skin-compatible, foam improving agents in liquid detergents and body cleansing compositions, and are present in an amount from about 1% to 15%, in particular from 1% to 10% by weight, calculated to the total composition.

Mixtures of anionic surfactants and alkyl polyglucosides as well as the use thereof in liquid body cleansing compositions are already known, for example, from EP-A 70 074. The alkyl polyglucosides disclosed therein are basically also suited within the scope of the present invention; as well as the mixtures of sulfosuccinates and alkyl polyglucosides disclosed in EP-A 358 216.

Further nonionic surfactant components may be present, for example, long-chain fatty acid dialkanolamides, such as coco fatty acid diethanolamide and myristic fatty acid diethanolamide, which can also be used as foam enhancers, preferably in amounts from about 1% to about 5% by weight.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Further suitable nonionic surfactants are amineoxides which may be present in an amount from 0.25% to 5% by weight, calculated to the total composition. Such amineoxides are state of the art, for example $C_{12}$-$C_{18}$-alkyl dimethyl amineoxides such as lauryl dimethyl amineoxide, $C_{12}$-$C_{18}$-alkyl amidopropyl or -ethyl amineoxides, $C_{12}$-$C_{18}$-alkyl di(hydroxyethyl) or (hydroxypropyl)amineoxides, or also amineoxides with ethyleneoxide and/or propyleneoxide groups in the alkyl chain. Such amineoxides are on the market, for example, under the trade names "Ammonyx®", "Aromox®" or "Genaminox®".

Further nonionic surfactants useful in the compositions according to invention are $C_{10}$-$C_{22}$-fatty alcohol ethoxylates at a concentration of 0.5 to 10%, preferably 0.5 to 5% by weight, calculated to total composition. Especially suited are $C_{10}$-$C_{22}$-fatty alcohol ethers, the alkyl polyglycol ethers known by the generic terms "Laureth", "Myristeth", "Oleth", "Ceteth", "Deceth", "Steareth" and "Ceteareth" according to the CTFA nomenclature, including addition of the number of ethylene oxide molecules, e.g., "Laureth-16":

The average degree of ethoxylation thereby ranges between about 2.5 and about 25, preferably about 10 and about 20.

The most preferred non-ionic surfactants are alkyl polyglucosides such as decyl, cocoyl polyglucoside and ethoxylated fatty alcohols such as laureth-16.

As further surfactant component, the compositions according to the invention can also contain amphoteric or zwitterionic surfactants, for example in an amount from about 0.5% to about 15%, preferably from about 1% to about 10%, by weight, calculated to the total composition. It has especially been found out that addition of zwitterionic or amphoteric surfactants enhances foam feeling in terms of creaminess, foam volume and as well as skin compatibility is improved. For achieving milder formulations anionic surfactant, especially of sulphate types, to amphoteric surfactant ratio should be in the range of 10:1 to 1:1, preferably 5:1 to 1:1.

Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

In detail, it is possible to use betaines of the structure

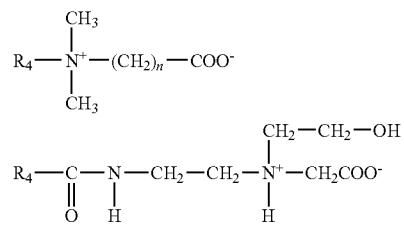

wherein $R_4$ is a $C_8$-$C_{18}$-alkyl group and n is 1 to 3;
sulfobetaines of the structure

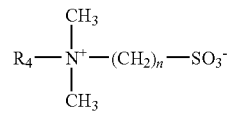

wherein $R_4$ and n are same as above;
and amidoalkyl betaines of the structure

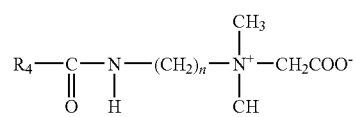

wherein $R_9$ and n are same as above.

The most preferred amphoteric surfactants are alkyl betaines such as lauryl betaine and alkyl amido betaines such as cocamidopropyl betaine.

In the preferred form of the present invention, cleansing composition comprises at least one anionic surfactant especially of alkyl ether sulphate type, at least one amphoteric surfactant especially alkyl amido alkyl betaine type and at least one non-ionic surfactant especiyll an alkyl polyglucoside. In the most preferred form of the present invention, in addition to the above mentioned surfactant the composition comprises additionally acyl amino carboxylic acid surfactant especially sodium lauroyl glutamate.

The composition of the present invention comprises hair-conditioning agents. Conditioning agents can be selected from oily substances, non-ionic substances, cationic amphiphilic ingredients, cationic polymers or their mixtures.

Oily substances are selected from such as silicone oils, either volatile or non-volatile, natural and synthetic oils. Among silicone oils those can be added to the compositions include dimethiconol, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Non-ionic conditioning agents may be polyols such as glycerin, glycol and derivatives, polyethyleneglycoles known with trade names Carbowax PEG from Union Carbide and Polyox WSR range from Amerchol, polyglycerin, polyethyleneglycol mono or di fatty acid esters having general formula $R_5CO(OCH_2CH_2)_nOH$ or $R_5CO(OCH_2CH_2)_nOOC\ R_6$ where $R_5$ and $R_6$ are independent from each other saturated, unsaturated or branched or non-branched alkyl chain with 7 to 21 C atoms and n is typically 2-100.

In one of the preferred from of the present invention, coloring enhancing cleansing compositions comprise at least one cationic polymer as conditioning agent. Suitable cationic polymers are those of best known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 37.

As well those polymers known with their CTFA category name Quaternium are suitable. Those are for example Quaternium-8, Quaternium-14, Quaternium-15, Quaternium-18, Quaternium-22, Quaternium-24, Quaternium-26, Quaternium-27, Quaternium-30, Quaternium-33, Quaternium-53, Quaternium-60, Quaternium-61, Quaternium-72, Quaternium-78, Quaternium-80, Quaternium-81, Quaternium-81, Quaternium-82, Quaternium-83 and Quaternium-84.

It has further been found out that especially those of cationic cellulose type polymers known as Polymer JR type from Amerchol such as Polyquaternium 10 or cationic guar gum known with trade name Jaguar from Rhône-Poulenc and chemically for example Guar hydroxypropyl trimonium chloride, are preferred ones. Furthermore, chitosan and chitin can also be included in the compositions as cationic natural polymers. In this context reference is also made to the cationic polymers disclosed in DE 25 21 960, 28 11 010, 30 44 738 and 32 17 059, as well as to the products described in EP-A 337 354 on pages 3 to 7. It is also possible to use mixtures of various cationic polymers.

The most preferred cationic polymers are those of cationic cellulose derivatives, cationic guar gum derivatives, polyquaternium 6 and polyquaternium 7.

The cationic polymers also include the quaternized products of graft polymers from organopolysiloxanes and polyethyl oxazolines described in EP-A 524 612 and EP-A 640 643.

Although less preferred cleansing compositions of the present invention may comprise additionally one or more cationic surfactant(s) as conditioner presented with the general formula $$R_7-\underset{\underset{R_{10}}{|}}{\overset{\overset{R_8}{|}}{N^+}}-R_9\ X^-$$

where $R_7$ is a saturated or unsaturated, branched or non-branched alkyl chain with 8-22 C atoms or $R_{11}CONH(CH_2)_n$ where $R_{11}$ is saturated or unsaturated, branched or non-branched alkyl chain with 7-21 C atoms and n has value of 1-4, or $R_{12}COO(CH_2)_n$ where $R_{12}$ is saturated or unsaturated, branched or non-branched alkyl chain with 7-21 C atoms and n has value of 1-4, and $R_8$ is hydrogen or unsaturated or saturated, branched or non-branched alkyl chain with 1-4 C atoms or $R_{11}CONH(CH_2)_n$ or $R_{12}COO(CH_2)_n$ where $R_{11}$, $R_{12}$ and n are same as above.

$R_9$ and $R_{10}$ are hydrogen or lower alkyl chain with 1 to 4 carbon atoms, and X is anion such as chloride, bromide, methosulfate.

Typical examples of those ingredients are cetyl trimethly ammonium chloride, stear trimonium chloride, behentrimoinium chloride, stearamidopropyl trimonuim chloride, dioleoylethyl dimethyl ammonium methosulfate, dioleoylethyl hydroxyethylmonium methosulfate.

The compositions according to the invention may also comprise further conditioning substances such as protein hydrolyzates and polypeptides, e.g., keratin hydrolyzates, collagen hydrolyzates of the type "Nutrilan®" or elastin hydrolyzates, as well as also in particular plant protein hydrolyzates, optionally, cationized protein hydrolyzates, e.g., "Gluadin®".

Typical concentration range for any of those conditioners of cationic polymers, silicon oil and derivatives and cationic surfactants can be 0.01-5% by weight, preferably 0.01-3.5% by weight, more preferably 0.05-2.5% and most preferably 0.1-1.5% by weight calculated to the total composition.

Further conditioning additives are hair conditioning and/or styling polymers. These may be nonionic polymers, preferably alcohol- and/or water-soluble vinyl pyrrolidone polymers, such as a vinyl pyrrolidone homopolymers or copolymers, in particular with vinyl acetate. Useful vinyl pyrrolidone polymers are, e.g., those known by the trade name "Luviskol®", for example, the homopolymers "Luviskol® K 30, K 60 and K 90", as well as the water-or alcohol-soluble copolymers from vinyl pyrrolidone and vinyl acetate, distributed by BASF AG under the trade name "Luviskol® VA 55 respectively VA 64". Further possible nonionic polymers are vinyl pyrrolidone/vinyl acetate/vinyl propionate copolymers such as "Luviskol® VAP 343", vinyl pyrrolidone/(meth)acrylic acid ester copolymers, as well as chitosan derivatives.

Amphoteric polymers are found to be useful in conditioning shampoo composition of the present invention. They are incorporated alone or in admixture with at least one additional cationic, nonionic or anionic polymer, particularly copolymers of N-octyl acrylamide, (meth)acrylic acid and tert.-butyl aminoethyl methacrylate of the type "Amphomer®"; copolymers from methacryl oylethyl betaine and alkyl methacrylates of the type "Yukaformer®", e.g., the butyl methacrylate copolymer "Yukaformer® Am75"; copolymers from monomers containing carboxyl groups and sulfonic groups, e.g., (meth)acrylic acid and itaconic acid, with monomers such as mono- or dialkyl amino alkyl(meth)acrylates or mono- or dialkyl aminoalkyl(meth)acrylamides containing basic groups, in particular amino groups; copolymers from N-octyl acryl-amide, methyl methacrylate, hydroxypropyl methacrylate, N-tert.-butyl aminoethyl-methacrylate and acrylic acid, as well as the copolymers known from U.S. Pat. No. 3,927,199, are applicable.

Cleansing composition of the present invention may comprise pearlizing agent. The preferred once are PEG-3 distearate and ethylene glycol distearate. The concentration of those can typically be from 0.1 to 3%, preferably 0.5 to 2% by weight, calculated to the total composition. These compounds are preferably added to the compositions in admixture with anionic, nonionic and/or amphoteric surfactants. Such kind of mixtures are available commercially.

Cleansing composition of the present invention may comprise organic solvents such as ethanol, propanol, isopropanol, benzyl alcohol, benzyloxyethanol, ethoxydiglycol, alkylene carbonates such as ethylene carbonate and propylene carbonate, phenoxyethanol, butanol, isobutanol, cyclohexane, cyclohexanol, hexyleneglycol, ethylenecarbonate, propyleneglycol, poypropyleneglycols, ethyleneglycol monoethylether, ethylene glycol monobutyl ether, ethylene glycol monophenyl ether, 1-phenylethylalcohol, 2-phenylethylalcohol, o-methoxyphenol. The most preferred ones are benzyloxyethanol and polypropylene glycols. Concentration of organic solvents in the shampoo composition should not exceed 5% by weight, preferably in the range of 0.1 to 3%, more preferably 0.25 to 2.5% by weight calculated to total composition. It should be kept in mind that the presence of the organic solvents may reduce foam performance of the cleansing composition which may be corrected either by carefully adjusting the concentration of organic solvent or increasing slightly the concentration of surfactants especially of anionic types.

Solubilizers may be added to the compositions especially when oily substances are chosen as conditioning agents and fragrance oils with highly lipophilic properties. Typical solubilizers may be hydrogenated castor oil known with the trade mark Cremophor CO series from BASF. It should be noted that as well the surfactant mixture can be a good solubilizer for fragrance oils. Typical concentration of the solubilizers can be in the range of 0.01-2% by weight, preferably 0.1-1% by weight, calculated to total composition.

The cleansing composition may contain active ingredients selected from UV filters, moisturisers, sequestering agents, and natural ingredients.

The moisturizing agents are selected from panthenol, polyols, such as glycerol, polyethylene glycols with molecular weight 200 to 20,000. The moisturizing ingredients can be included in the conditioner compositions at a concentration range of 0.01-2.5% by weight calculated to the total composition.

The sequestering agents are preferably selected from polycarboxy acids. The preferred one is ethylene diamine tetraacetic acid, EDTA. Typical useful concentration range for sequestering agents is of 0.01-2.5% by weight calculated to the total composition.

The UV filters are those oil and water soluble ones for the purpose of protecting hair colour. In other words, anionic and nonionic, oily, UV filters are suitably used in the compositions of the present invention. Suitable UV-absorbing substances is are: Poly<silicone-15, 4-Aminobenzoic acid and the esters and salts thereof, 2-phenyl benzimidazole-5-sulfonic acid and the alkali and amine salts thereof, 4-dimethyl aminobenzoic acid and the esters and salts thereof, cinnamic acid and the esters and salts thereof, 4-methoxycinnamic acid and the esters and salts thereof, salicylic acid and the esters and salts thereof, 2,4-dihydroxybenzophenone, 2,2',4,4'-tetrahydroxy-benzophenone, 2-hydroxy-4-methoxybenzophenone and its 5-sulfonic acid or the sodium salt thereof, 2,2'-dihydroxy-4,4'-dimethoxybenzophenone, 2-hydroxy-5-chlorobenzophenone, 2,2'-dihydroxy-4-methoxybenzophenone, 2,2'-dihydroxy-4,4'-dimethoxy-5,5'-disulfobenzo-phenone or the sodium salt thereof, 2-hydroxy-4-octyloxybenzophenone, 2-hydroxy-4-methoxy-4'-methylbenzophenone, 3-benzyl-idenecampher, 3-(4'-sulfo)-benzyl-idenebornane-2-one and the salts thereof and/or 3-(4'-methyl benzylidene)-DL-campher. The amount of the UV-absorber ranges typically from about 0.01% to 2.5%, more preferably from 0.05% to 1% by weight, calculated to the total composition.

Natural plant extracts are incorporated usually in an amount of about 0.01% to about 10%, preferably 0.05% to 7.5%, in particular 0.1% to 5% by weight, calculated as dry residue thereof to the total composition. Suitable aqueous (e.g. steam-distilled) alcoholic or hydro-alcoholic plant extracts known per se are in particular extracts from leaves, fruits, blossoms, roots, rinds or stems of aloe, pineapple, artichoke, arnica, avocado, valerian, bamboo, henbane, birch, stinging nettle, echinacea, ivy, wild angelica, gentian, ferns, pine needles, silver weed, ginseng, broom, oat, rose hip, hamamelis, hay flowers, elderberry, hop, coltsfoot, currants, chamomile, carrots, chestnuts, clover, burr root, cocoanut, cornflower, lime blossom, lily of the valley, marine algae, balm, mistletoe, passion flower, ratanhia, marigold, rosemary, horse chestnut, pink hawthorn, sage, horsetail, yarrow, primrose, nettle, thyme, walnut, wine leaves, white hawthorn, etc. Suitable trade products are, for example, various "Extrapone®" products, and "Herbasol®". Extracts and the preparation thereof are also described in "Hagers Handbuch der pharmazeutischen Praxis", $4^{th}$ Ed.

The viscosity of the cleansing compositions according to the invention is in the range of 500 and about 20,000 mPa·s at 20° C., preferably 1,000 to 10,000, in particular 1,000 to 7,000 mPa·s at 20° C., measured with Brookfield or Höppler viscosimeters at a shear rate of 10 $sec^{-1}$.

Viscosity of shampoo compositions can be adjusted with known viscosity enhancers. The preferred ones are PEG-55 propyleneglycol oleate and PEG-18 glyceryl oleate/cocoate known with the trade names Antil® 141 and 171, respectively and PEG-160 sorbitan triisostearate known with a trade name Rheodol®. It should be noted that in the case that a composition is delivered in the form of a foam from a pump-foamer and/or aerosol can, those compositions should not be thickened and have a viscosity value not more than 500 mPa·s, more preferably 250 mPa·s measured as mentioned above at room temperature.

It is self-understood that the shampoos according to the invention may comprise other substances customarily used in such compositions such as preservatives, fragrances.

The following examples are to illustrate the invention, but not to limit. The products according to the invention are prepared by mixing the individual components in water, whereby it is also possible to use pre-mixtures of various ingredients.

EXAMPLE 1

|  | % by weight |
| --- | --- |
| Sodium lauryl ether sulphate | 8.0 |
| Cocoyl polyglucoside | 3.0 |
| Cocamidopropyl betaine | 3.0 |
| Sodium lauroyl glutamate | 1.0 |
| Polyquaternium-10 | 1.0 |
| Synthetic fluorphologopite* | 1.0 |
| Citric acid/sodium hydroxide | q.s. to pH 5.5 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 µm.

For comparative purposes the above composition was also produced without Synthetic fluorphologopite.

The above composition was prepared by combining surfactants with part of water and subsequently adding Polyquaternium-10 solution in water prepared at around 70° C. Afterwards, Synthetic fluorphologopite dispersed in small portion of water was added and preservative and fragrance was mixed. Finally pH was adjusted.

The performance of example was compared to the comparative composition in a half side test with 10 volunteers. Hair of the volunteer was divided into 2 and washed with example 1 and comparative composition using according to hair length 4 to 6 g of the product. After rinsing both sides were evaluated by at least 2 hair dressers and by the volunteer in towel dried and dry state. It was found that the side washed with example 1 had more elasticity, more volume and body and especially significantly more shine. The preference was generally 8 to 2 and for shine 10/0.

Similar results were observed with the examples below.

EXAMPLE 2

|  | % by weight |
| --- | --- |
| Sodium lauryl ether sulphate | 8.0 |
| Laureth-16 | 3.0 |
| Cocamidopropyl betaine | 3.0 |
| Sodium lauroyl glutamate | 1.0 |
| Polyquaternium-7 | 1.0 |
| Dimethicone | 0.4 |
| PEG-18 glyceryl oleate/cocoate | 1.0 |
| Synthetic fluorphologopite* | 1.0 |
| Citric acid/sodium hydroxide | q.s. to pH 5.5 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 µm.

The above composition was prepared in the similar way as example 1.

EXAMPLE 3

|  | % by weight |
| --- | --- |
| Sodium lauryl ether carboxylate | 9.0 |
| Laureth-16 | 3.0 |
| Cocoyl betaine | 2.0 |
| Sodium lauroyl glutamate | 2.0 |
| Polyquaternium-6 | 1.0 |
| Amodimethicone | 0.4 |
| PEG-18 glyceryl oleate/cocoate | 1.0 |
| Synthetic fluorphologopite* | 1.0 |
| Citric acid/sodium hydroxide | q.s. to pH 5.0 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 µm.

EXAMPLE 4

|  | % by weight |
| --- | --- |
| Sodium lauryl ether sulphate | 8.0 |
| Cocoyl polyglucoside | 3.0 |
| Cocoamphoacetate | 4.0 |
| Polyquaternium-10 | 1.0 |
| Synthetic fluorphologopite* | 1.0 |
| Citric acid/sodium hydroxide | q.s. to pH 5.5 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 µm.

EXAMPLE 5

|  | % by weight |
| --- | --- |
| Sodium lauryl ether carboxylate | 9.0 |
| Laureth-16 | 3.0 |
| Cocoyl betaine | 2.0 |
| Sodium lauroyl glutamate | 2.0 |
| Guarhydroxypropyltrimonium chloride | 1.0 |
| PEG-18 glyceryl oleate/cocoate | 1.0 |
| Synthetic fluorphologopite* | 1.0 |
| Citric acid/sodium hydroxide | q.s. to pH 5.0 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 µm.

EXAMPLE 6

|  | % by weight |
| --- | --- |
| Sodium lauryl ether carboxylate | 9.0 |
| Laureth-16 | 3.0 |
| Cocoyl betaine | 2.0 |
| Sodium lauroyl glutamate | 2.0 |
| Dimethicone | 2.5 |
| Carbomer | 1.0 |

-continued

| | % by weight |
|---|---|
| Synthetic fluorphologopite* | 1.0 |
| Citric acid/sodium hydroxide | q.s. to pH 5.0 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 μm.

EXAMPLE 7

| | % by weight |
|---|---|
| Sodium lauryl ether carboxylate | 9.0 |
| Laureth-16 | 3.0 |
| Cocoyl betaine | 2.0 |
| Sodium lauroyl glutamate | 2.0 |
| Dimethicone | 2.5 |
| Carbopol Aqua SF1 | 1.0 |
| Synthetic fluorphologopite* | 1.0 |
| Citric acid/sodium hydroxide | q.s. to pH 5.0 |
| Preservative, fragrance | q.s |
| Water | to 100 |

*Synthetic fluorphologopite used is commercially available from Sun Chemical Corporation under the trade name SunShine Glitter White with a particle size distribution in the range of 20 to 95 μm.

The invention claimed is:

1. A keratin fiber cleansing composition comprising:
    a) from 5 to 50% by weight calculated to total composition of a surfactant system comprising:
        i) an aminocarboxylic acid anionic surfactant;
        ii) a non-ionic surfactant; and
        iii) an amphoteric surfactant, wherein the surfactant system does not contain any monoethanolamide surfactant; and
    b) from 0.001 to 10% by weight calculated to total composition at least one color effect pigment consisting of synthetic fluorphologopite coated with metal oxide or oxides and having a volume particle size distribution in the range of 1 to 750 μm.

2. Composition according to claim 1, wherein the color effect pigment has a volume particle size distribution in the range of 20 to 95 μm.

3. Composition according to claim 1, further comprising at least one conditioning agent.

4. Composition according to claim 1, further comprising at least one thickener.

5. Composition according to claim 1, further comprising comprises at least one UV filter.

6. Composition according to claim 1, further comprising at least one pearlising agent.

7. Composition according to claim 1, further comprising at least one organic solvent.

* * * * *